US00PP15770P2

(12) United States Plant Patent
Craig

(10) Patent No.: US PP15,770 P2
(45) Date of Patent: May 17, 2005

(54) **REGAL *PELARGONIUM* NAMED 'ELEGANCE SILVER'**

(50) Latin Name: *Pelargonium×domesticum*
Varietal Denomination: Elegance Silver

(75) Inventor: Richard Craig, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 1 day.

(21) Appl. No.: 10/811,495

(22) Filed: Mar. 26, 2004

(51) Int. Cl.[7] ..... A01H 5/00
(52) U.S. Cl. ..... Plt./331
(58) Field of Search ..... Plt./331

*Primary Examiner*—Kent Bell
(74) *Attorney, Agent, or Firm*—Webb Ziesenheim Logsdon Orkin & Hanson, P.C.

(57) ABSTRACT

A new and distinct regal *geranium* plant with white flowers having purple feathering above medium green foliage. The new cultivar exhibits extended flower longevity.

3 Drawing Sheets

Botanical classification: *Pelargonium×domesticum.*
Varietal denomination: 'Elegance Silver'.

BACKGROUND OF THE INVENTION

This discovery relates to a new and distinct cultivar of regal *Pelargonium* (*Pelargonium×domesticum*) identified by the name of 'Elegance Silver', Breeder No. 99-128-01 and Oglevee, Ltd. No. 629. The cultivar was discovered in an organized, scientifically designed breeding program conducted at the Department of Horticulture, The Pennsylvania State University, University Park, Pa. The purpose of the breeding program was to create new regal *Pelargonium* genotypes with clear, bright flower colors, excellent propagation characteristics, compact growth habit, predictable and consistent flowering response and excellent postharvest quality. The new cultivar is compact, self-branching (without pinching) and early flowering. The flowers are white with a slight purple feather. The most outstanding trait of this new cultivar is its extended floral longevity.

The pistillate parent (Breeder No. 95-9-4) is a cross-pollination of 'Duchess' (U.S. Plant Pat. No. 8,074) and Breeder No. 93-11-5 produced according to the pedigree appearing in FIG. 2. The staminate parent (Breeder No. 95-10-3) was developed from prior selections at The Pennsylvania State University since 1977 according to the pedigree appearing in FIG. 3. In the pedigrees of FIGS. 2 and 3, the first two digits refer to the year that the entry originated.

Two seeds of this hybrid were sown on Mar. 31, 1999 and were identified as Breeder No. 99-128. One of the seeds germinated and the seedling (Breeder No. 99-128-1) was grown to maturity and produced its first inflorescence on Aug. 28, 1999. This seedling was judged to be pollen fertile, have attractive flowers and to display limited flower production.

This seedling was cultivated to produce a stock plant for harvesting asexual propagules. The selection was asexually propagated by cuttings on Oct. 14–15, 1999 at University Park, Pa. These cuttings were placed into a mist facility and one cutting produced roots. This cutting was floral initiated and grown to maturity. Initial data were recorded on Feb. 25, 2000. The plant was judged to have very good foliage, small height, good branching, very good flowering, and overall was judged very good. Three similar trials were evaluated in the spring (greenhouse) and summer (garden) of 2000. All of the reproductions ran true. Subsequent evaluations were conducted in the greenhouse (five times annually) and garden (annually) in 2001, 2002 and 2003. The new cultivar was trial and field tested in Connellsville, Pa. and was found to retain its characteristics through successive asexual generations.

The description of the new cultivar that is presented below was developed from plants grown in a glass greenhouse in Connellsville, Pa. Rooted cuttings were potted into 5" or 6" plastic Azalea pots containing a 80% peat and 20% Perlite medium with a pH of 6.0–6.8. The plants were grown for two weeks to establish a vigorous root system. Environmental conditions were 62–64° F. at night and ventilation in the day when temperatures reached 70° F. A soluble fertilizer delivering 150 ppm of nitrogen and potassium was used at each irrigation. At the end of two weeks, the plants were moved to a floral initiation environment for four weeks that was maintained at 54° F. The area included supplemental irradiance of 560 footcandles (fc) of High Intensity Discharge (HID) lighting accomplished with high pressure sodium lamps from 700 to 2300 hours daily (16 hours). The lamps were not used when natural irradiance was above 660 fc at plant level. In addition long photoperiods were established with the application of 40 fc of incandescent lamps for 16 hours daily; lamps were on for 15 minutes and off for 45 minutes each hour. Plants were subjected to water stress during this time. At the end of four weeks the plants were moved to a forcing environment that was maintained at 60° F. at night and ventilated in the day when temperatures reached 67° F. Supplemental irradiance was applied at 200 fc HID, as described above, from 700–2300 hours. No chemical growth regulators were applied.

DESCRIPTION OF THE PLANT

Figure 1:
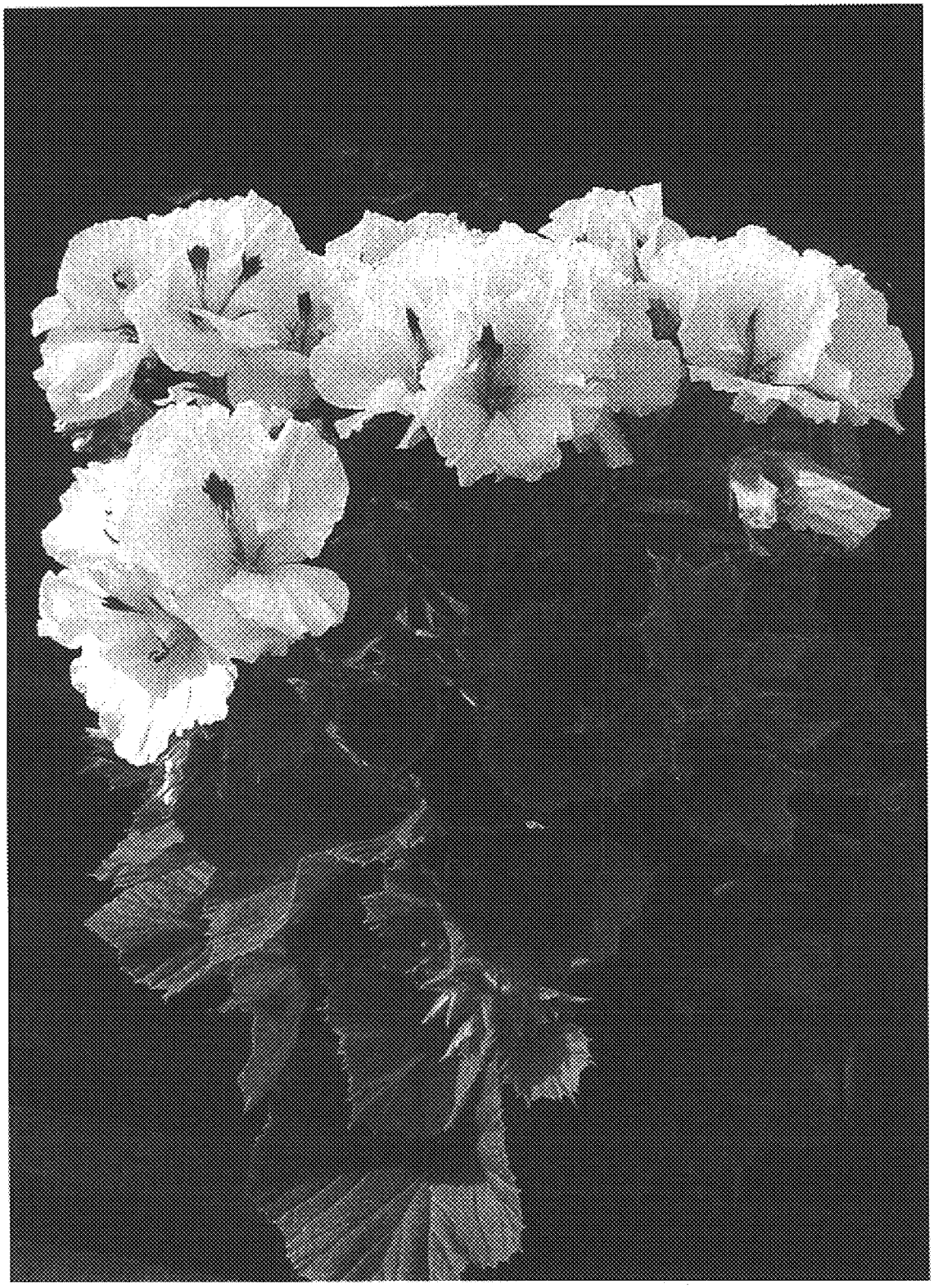
FIG. 1 is a photographic drawing illustrating the new cultivar with the color being as nearly true as is possible with color illustrations of this type.
Figure 2:
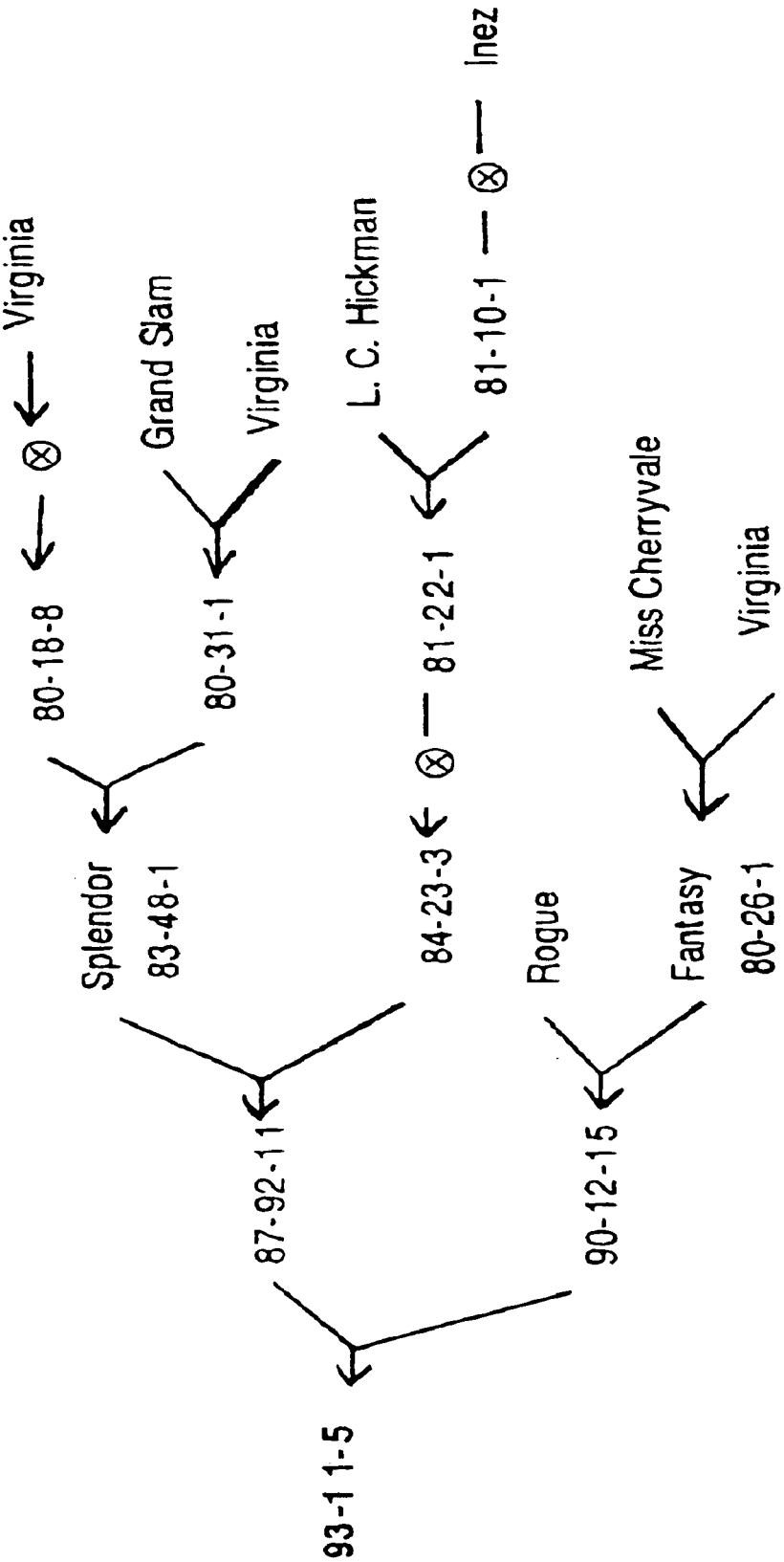
FIG. 2 shows the pedigree of the pistillate parent.
Figure 3:
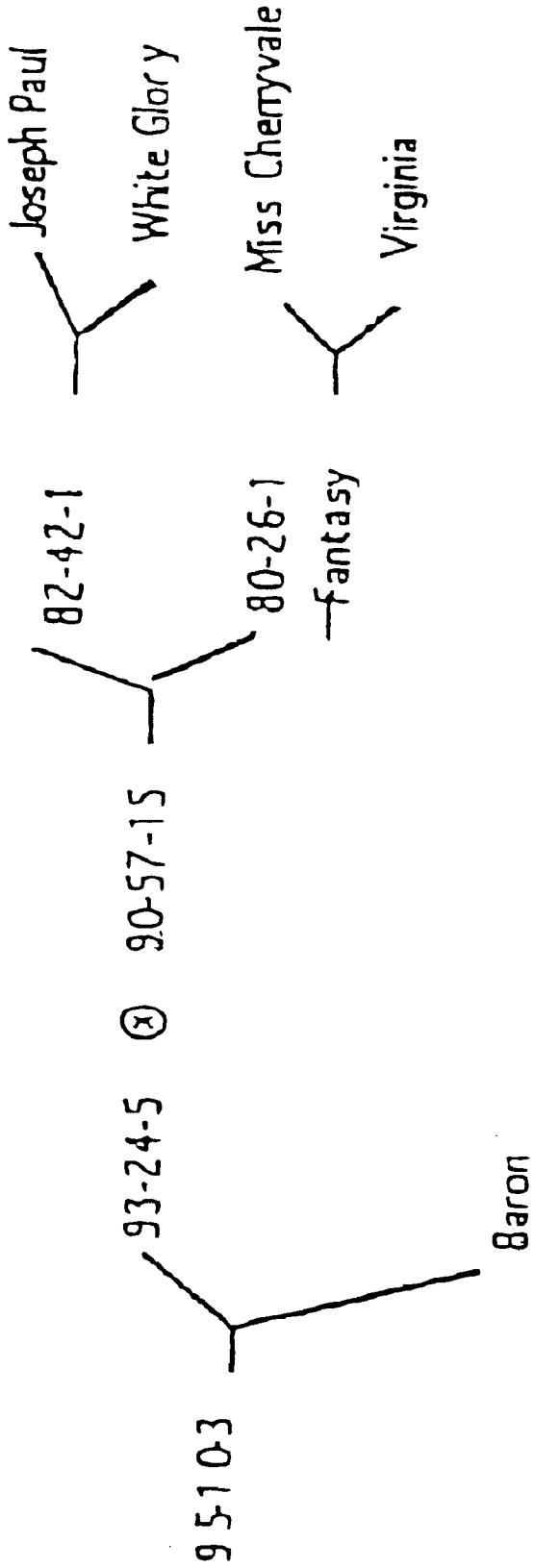
FIG. 3 shows the pedigree of the staminate parent.

The following detailed description set forth the characteristics of the new cultivar. The data which defines these characteristics were collected from asexual reproductions carried out in Connellsville, Pa. The color readings on a plant grown in a 5-inch pot were taken indoors under 200–220 footcandles of cool white fluorescent light. Color references are primarily to The R.H.S. Colour Chart of The Royal Horticultural Society of London.

THE PLANT

Classification:
- *Botanical.*—*Pelargonium×domesticum.*
- *Commercial.*—Regal *pelargonium.*

Form: Medium mound.
Height: 20.0–26.0 cm from soil to top of foliage.
Diameter: 20 cm to 26 cm.
Growth: Medium mound habit with free basal branching; continuous flowering.
Foliage: Stalked leaf attachment.
Leaves:
- *Size.*—5.9–11.9 cm across 5.2 cm to 8.5 cm long.
- *Shape.*—Reniform, truncate base.
- *Margin.*—Serrated, slightly lobed.
- *Texture.*—Rough, pubescent.
- *Color.*—Upper surface: Green Group 137C. Lower surface: Green Group 138B. Zone: None.
- *Ribs and veins.*—Venation: Palmate. Color: Yellow Green Group 147C.
- *Petioles.*—Length: 2.0–5.5 cm. Color: Yellow Green Group 146C.
- *Stem.*—Color: Yellow Green Group 146C. Internode length: 1.5–2.5 cm. Length: 6.0 cm to 8.0 cm.

THE BUD

- *Shape when just showing color.*—Elliptical.
- *Size when just showing color.*—1.5–2.0 cm long and 0.7 cm wide; 2.8–5.6 cm across overall cluster.
- *Buds per cluster.*—3 to 12.

INFLORESCENCE

Blooming habit: Large flower forming full inflorescences.
Borne: Flower on pedicel, pedicel on peduncle.
Open flower:
- *Form.*—Open to slightly cupped; petals overlap; edges ruffled.
- *Size of fully open bloom.*—Umbels: Width: 8.5–11.5 cm. Depth: 6.9–8.0 cm. Flowers: Length: 4.0–4.5 cm. Width: 5.3–7.0 cm. Depth: 2.1–2.8 cm.

Petals:
- *Color.*—Upper surface: Close to White Group 155D with pearlescent finish. The upper two petals have a petal base tipped in Purple Group 64B. Lower surface: Lower petals: White Group 155D. Upper two petals: Base color of White Group 155D with two 'y' shaped veins of Purple Group 64A. A shadow of the top surface can be seen due to the opaque quality of the petal. The base of each of these two petals is tipped in Purple Group 64B. Feather blotch (upper surface): Present on upper two petals: center feather blotch is solid Gray Purple Group 187A bleeding into the veins of the feather that are Purple Group 64A edged in Purple Group 64B.
- *Quantity.*—5–6.
- *Appearance.*—Clear white blossoms with upper petals feathered in purple displayed above medium green foliage.

Petaloids: None.
Pedicel:
- *Length.*—2.0–2.5 cm.
- *Color.*—Green Group 137B at base of flower with the rest of the pedicel being Green Group 137C.

Peduncle:
- *Length.*—4.5–6.0 cm.
- *Color.*—Green Group 137C.

Disease resistance: No susceptibility to diseases or pests has been noted to date.

REPRODUCTIVE ORGANS

Stamens:
- *Anthers.*—2.0–3.0 mm long.
- *Filaments.*—Length: 1.0–1.5 cm. Color: White Group 155D.
- *Pollen color.*—Grayed Orange Group 169D.

Pistils:
- *Number.*—1; five parted.
- *Length.*—1.5 cm.
- *Stigma color.*—Red Purple Group 64A.
- *Style.*—1.1 cm long.
- *Ovaries.*—Length: 5.0–6.0 mm. Width: 2.0 mm. Color: Grayed Green Group 191B.
- *Fruit.*—None observed.

GENERAL CHARACTERISTICS

This cultivar is characterized by having greatly improved postharvest floral longevity in the greenhouse, in market channels and in the consumer environment over other varieties in this market class known to the inventor.

I claim:

1. A new and distinct cultivar of *geranium* plant substantially as shown and described.

* * * * *

UNITED STATES PATENT AND TRADEMARK OFFICE

CERTIFICATE OF CORRECTION

PATENT NO. : PP 15,770 P2
DATED : May 17, 2005
INVENTOR(S) : Richard Craig

It is certified that error appears in the above-identified patent and that said Letters Patent is hereby corrected as shown below:

Column 3,
Line 43, under "INFLORESCENCE", after "Blooming Habit," delete "Large flower forming full inflorescences." and insert -- 3 to 12 flowers per inflorescence. --.

Signed and Sealed this

Seventeenth Day of January, 2006

JON W. DUDAS
*Director of the United States Patent and Trademark Office*

UNITED STATES PATENT AND TRADEMARK OFFICE

CERTIFICATE OF CORRECTION

PATENT NO. : PP15,770 P2
APPLICATION NO. : 10/811495
DATED : May 17, 2005
INVENTOR(S) : Richard Craig It is certified that error appears in the above-identified patent and that said Letters Patent is hereby corrected as shown below:

The following paragraph should be inserted on the Cover Page of the Patent, and at Column 1, immediately before "BACKGROUND OF THE INVENTION":

--STATEMENT REGARDING FEDERALLY SPONSORED RESEARCH
This invention was made with government support under Hatch Act Project No. PEN03569, awarded by the United States Department of Agriculture (USDA). The Government has certain rights in the invention.--

Signed and Sealed this
Twenty-fifth Day of January, 2011

David J. Kappos

David J. Kappos
*Director of the United States Patent and Trademark Office*